(12) United States Patent
Lemchen

(10) Patent No.: US 10,473,942 B2
(45) Date of Patent: Nov. 12, 2019

(54) APPARATUS AND METHOD FOR IMAGE CAPTURE OF MEDICAL OR DENTAL IMAGES USING A HEAD MOUNTED CAMERA AND COMPUTER SYSTEM

(71) Applicant: Marc Lemchen, New York, NY (US)

(72) Inventor: Marc Lemchen, New York, NY (US)

(*) Notice: Subject to any disclaimer, the term of this patent is extended or adjusted under 35 U.S.C. 154(b) by 493 days.

(21) Appl. No.: 14/732,483

(22) Filed: Jun. 5, 2015

(65) Prior Publication Data

US 2016/0358327 A1    Dec. 8, 2016

(51) Int. Cl.

| G02B 27/01 | (2006.01) |
| H04N 5/232 | (2006.01) |
| A61B 1/04 | (2006.01) |
| A61B 1/24 | (2006.01) |
| A61B 1/00 | (2006.01) |
| A61B 90/50 | (2016.01) |

(52) U.S. Cl.
CPC ...... *G02B 27/0179* (2013.01); *A61B 1/00048* (2013.01); *A61B 1/04* (2013.01); *A61B 1/24* (2013.01); *H04N 5/23287* (2013.01); *H04N 5/23293* (2013.01); *A61B 2090/502* (2016.02); *G02B 2027/0138* (2013.01); *G02B 2027/0178* (2013.01); *G06T 2207/30036* (2013.01); *H04N 5/23238* (2013.01); *H04N 5/23296* (2013.01)

(58) Field of Classification Search
CPC ........ G02B 27/0179; G02B 2027/0138; G02B 2027/0178; A61B 1/00048; A61B 1/04; A61B 1/24; A61B 2090/502; H04N 5/23287; H04N 5/23293; H04N 5/23238; H04N 5/23296; G06T 2207/30036
See application file for complete search history.

(56) References Cited

U.S. PATENT DOCUMENTS

| 8,643,951 B1* | 2/2014 | Wheeler | G06F 3/012 359/630 |
| 2006/0238877 A1* | 10/2006 | Ashkenazi | G02B 27/0093 359/630 |
| 2009/0244324 A1* | 10/2009 | Saito | H04N 5/23219 348/231.99 |
| 2011/0102549 A1* | 5/2011 | Takahashi | A61C 1/084 348/46 |
| 2013/0044042 A1 | 2/2013 | Olsson | |
| 2015/0085171 A1* | 3/2015 | Kim | H04N 13/344 348/333.04 |
| 2015/0173846 A1* | 6/2015 | Schneider | A61B 1/00009 600/424 |

(Continued)

*Primary Examiner* — Maria E Vazquez Colon
(74) *Attorney, Agent, or Firm* — Marcus C. Dawes; Daniel L. Dawes

(57) ABSTRACT

A head mounted magnifying camera is communicated with a computer system with a head-mounted display having a center of a field of view. A magnified view of a live dental area of interest is provided, image capture of the live dental area of interest is performed and downloaded into the computer system, or an image of a stored dental area of interest is uploaded from the computer system and matched to the live dental area of interest. The image of the live dental area of interest is automatically tracked in the computer system, and the image of the live dental area of interest is kept in the center of the field of view of the head-mounted display.

17 Claims, 2 Drawing Sheets

(56) References Cited

U.S. PATENT DOCUMENTS

| | | | |
|---|---|---|---|
| 2015/0207961 A1* | 7/2015 | Gavney, Jr. | G06K 9/3275 348/169 |
| 2015/0244903 A1* | 8/2015 | Adams | G02B 27/017 348/376 |
| 2016/0015470 A1* | 1/2016 | Border | G02B 27/017 600/117 |
| 2017/0099479 A1* | 4/2017 | Browd | H04N 13/044 |

* cited by examiner

APPARATUS AND METHOD FOR IMAGE CAPTURE OF MEDICAL OR DENTAL IMAGES USING A HEAD MOUNTED CAMERA AND COMPUTER SYSTEM

BACKGROUND

Field of the Technology

The invention relates to the field of dental loupes and image tracking and capture.

Description of the Prior Art

Google Glass is a wearable computer with an optical head-mounted display (OHMD). It was developed by Google with the mission of producing a mass-market ubiquitous computer. Google Glass displays information in a smartphone-like hands-free format. Wearers communicate with the Internet via natural language voice commands. Google Glass became officially available to the general public on May 15, 2014. The development and manufacture of head mounted computer displays, such as marketed under the brand, Google Glass, has made computer displays readily available to the computer user in a display unit mounted in a glasses frame. This allows the user to see and interact by appropriate means with a computer system, while simultaneously allowing the user operate both hands-free and to have substantially unimpeded view of any other field of view. Google Glass essentially duplicates an aviator's view of instrument readings on the cockpit glass or face shield while allowing simultaneous normal viewing through the same cockpit glass or face shield.

Using these features several proofs of concept for Google Glass have been proposed in healthcare. These uses have generally been used for audiovisual communication and information retrieval during a variety of medical procedures.

On Mar. 31, 2014, a startup company Dentyzion, founded by four dental students at the University of Michigan School of Dentistry, announced the world's first Google Glass loupes. The dental technology and digital marketing consulting company designed the add-on to Glass and collaborated with SurgiTel who manufactured the magnifying optics according to the model. The loupe lenses are critical for Glass' functionality in dentistry and surgery by allowing dentists and surgeons to continue to use magnification while using Google Glass. The design is reported to have been well received amongst dental students and faculty at the University of Michigan. SurgiTel's Micro 2.5× optics that were installed are light weight and do not affect the comfort and balance for Glass users. Dentyzion is currently collaborating with the University of Michigan to implement Google Glass in the dental curriculum. Dentyzion, however, merely mechanically mounted dental loupes into the frames of a Google Glass having a telescopic camera directed to the same or nearly the same field of view of the loupes for the purposes of creating an audiovisual source for use in and for enhancing dental education.

Users of dental loupes can readily testify that it takes practice and training to use them, since the magnified field of view seen through the loupes can rapidly change as the user moves his head. The problem becomes particularly acute, when the user changes his line of sight to another field of view other than that seen through the loupes and then returns his eyes to the field of view provided by the loupes. Typically, the angle or position of the head has changed enough when the user changes his line of sight, so that upon return to the field of view of the loupes, a completely different location is seen in magnified view than that which was being viewed before the user looked away. The user then has to move his head angle to hunt for the prior magnified field of view based on a magnified scene or view that may not be clearly related in the user's mind to the prior field of view which is desired. This hunting for the prior field of view is distracting and may entail wasted time and effort from the desired task at hand unless the user is practiced in mentally switching between scales and views in an effortless manner.

BRIEF SUMMARY

The illustrated embodiments of the invention include a method including the steps of providing a head mounted magnifying camera communicated with a computer system with a head-mounted display having a center of a field of view, providing a magnified view of a live dental area of interest, actuating image capture of the live dental area of interest and downloading it into the computer system, or uploading an image of a stored dental area of interest from the computer system and matching it to the live dental area of interest, automatically tracking the image of the live dental area of interest in the computer system, and keeping the image of the live dental area of interest in the center of the field of view of the head-mounted display.

The method further includes the step of automatically compensating for small movements of the head mounted magnifying camera shifting the center of the field of view by using a tracking program in the computer system to keep the live dental area of interest in the center of the field of view of the head-mounted display.

The method further includes the steps of providing a micro-pan and tilt mechanism coupled to the camera or a lens of the camera for larger movements of the head that take live dental area of interest out of the center of the field of view beyond that which can be compensated by the tracking program; and automatically moving the camera angle using the micro-pan and tilt mechanism to keep the live dental area of interest in the center of the field of view of the head-mounted display.

The step of automatically tracking the image of the live dental area of interest in the computer system includes the steps of providing a micro-pan and tilt mechanism coupled to the camera or a lens of the camera; and automatically moving the camera angle using the micro-pan and tilt mechanism to keep the live dental area of interest in the center of the field of view of the head-mounted display.

The method further the steps of storing a wide field of view around the image of the live dental area of interest that exceeds the range of the pan and tilt mechanism's ability to stay pointed at the live dental area of interest, displaying an "out-of-frame" message or icon in the head-mounted display, controlling the pan and tilt mechanism to direct the head-mounted camera to the live dental area of interest and/or displaying directional arrows in the head-mounted display to cue the user to the direction in which the head-mounted camera needs to be turned in order to bring the of the live dental area of interest toward the center of the field of view by using an image recognition program in the computer system using the stored wide field of view around the image of the live dental area of interest, reacquiring at least a portion of the wide field of view around the image of the live dental area of interest, identifying the desired live dental area of interest by the image recognition program, and moving the desired live dental area of interest into the center of the field of view using the tracking program.

The step of storing a wide field of view around image of the live dental area of interest includes taking and storing a fast image capture of an enhanced wide field of view using a telescopic camera control.

The step of storing the wide field of view is stored in a fast frame shot at the time of image capture during a time interval which is short enough so that the user does not perceive that the camera has taken a telescopic enhanced wide field of view image.

The step of storing a wide field of view around image of the live dental area of interest includes taking a high resolution wide angle image, but displaying only a center portion of the high resolution wide angle image in the head-mounted display in a magnified view.

The method further includes releasing or erasing the captured image by a deactivation command from the user.

The illustrated embodiments of the apparatus also include a computer system with a memory, a head mounted magnifying camera communicated with the computer system for providing a magnified image of a live dental area of interest, and a head-mounted display having a center of a field of view and communicated with the computer system, where the computer system automatically tracks the magnified image of the live dental area of interest to keep it in the center of the field of view of the head-mounted display, and where the memory stores a captured image of the live dental area of interest.

The computer system automatically compensates for small movements of the head mounted magnifying camera shifting the center of the field of view to keep the live dental area of interest in the center of the field of view of the head-mounted display by image tracking.

The apparatus further includes a micro-pan and tilt mechanism coupled to the camera or a lens of the camera for larger movements of the head that take live dental area of interest out of the center of the field of view beyond that which can be compensated by the tracking program, and the computer system automatically moves the camera angle using the micro-pan and tilt mechanism to keep the live dental area of interest in the center of the field of view of the head-mounted display by image tracking.

The apparatus further includes a micro-pan and tilt mechanism coupled to the camera or a lens of the camera; and the computer system automatically moves the camera angle using the micro-pan and tilt mechanism to keep the live dental area of interest in the center of the field of view of the head-mounted display by image tracking.

The computer system stores an image with a wide field of view around the image of the live dental area of interest that exceeds the range of the pan and tilt mechanism's ability to stay pointed at the live dental area of interest, displays an "out-of-frame" message or icon in the head-mounted display, controls the pan and tilt mechanism to direct the head-mounted camera to the live dental area of interest and/or displays directional arrows in the head-mounted display to cue the user to the direction in which the head-mounted camera needs to be turned in order to bring the of the live dental area of interest toward the center of the field of view using image recognition on the stored wide field of view around the image of the live dental area of interest, reacquires at least a portion of the wide field of view around the image of the live dental area of interest, identifies the desired live dental area of interest by image recognition, and moves the desired live dental area of interest into the center of the field of view by image tracking.

The computer system stores the wide field of view around image of the live dental area of interest by taking and storing a fast image capture of an enhanced wide field of view using a telescopic camera control.

The computer system takes and stores the fast image capture by taking a fast frame shot at the time of image capture during a time interval which is short enough so that the user does not perceive that the camera has taken a telescopic enhanced wide field of view image.

The computer system stores an image with a wide field of view around the image of the live dental area of interest by taking a high resolution wide angle image, but displaying only a center portion of the high resolution wide angle image in the head-mounted display in a magnified view.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
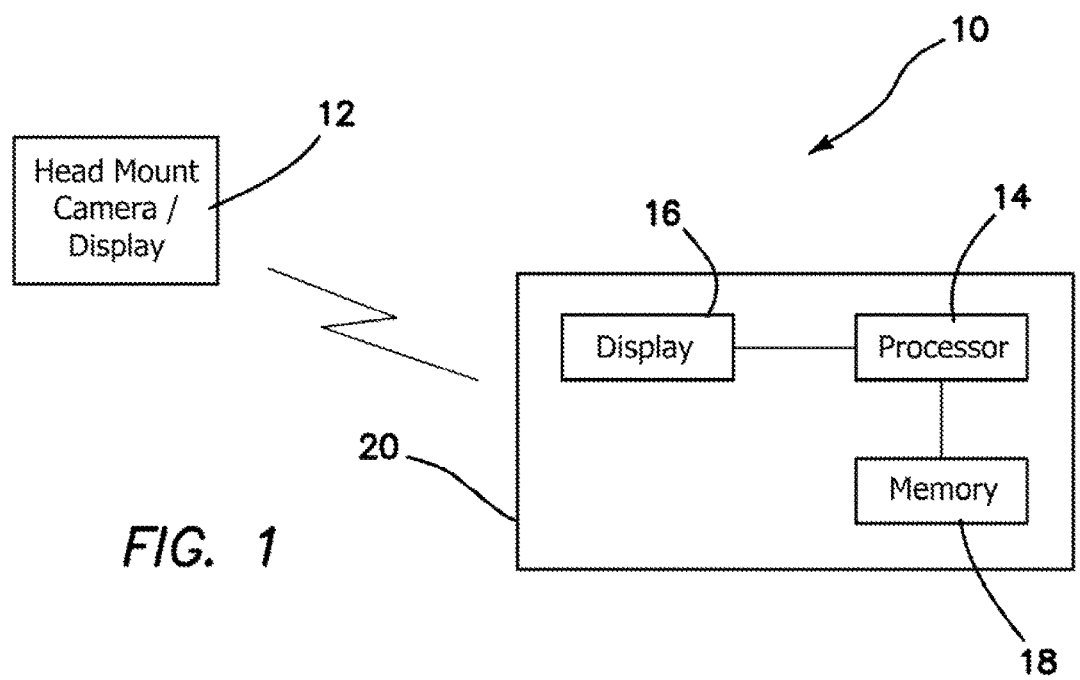
FIG. 1 is a block diagram of remote head-mounted camera and display subsystem wirelessly communicated with a computer system.
Figure 2:
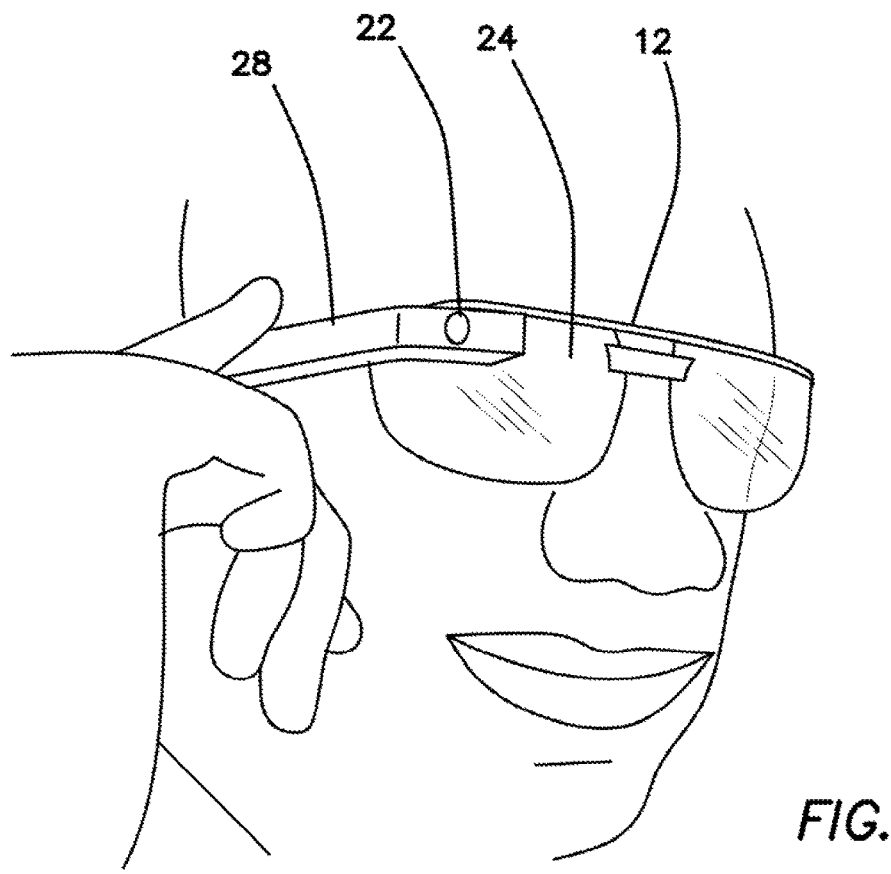
FIG. 2 is a depiction of a using wearing the head-mounted camera and display subsystem of FIG. 1.

In the illustrated embodiment of the invention the dental loupes are replaced by a head mounted magnifying camera communicated with a computer system with a head-mounted display, similar to that shown as Google Glass disclosed in US Pat. Pub. 2013/0044042 incorporated herein by reference, except that the camera is modified in various particulars as set forth below and its output is used to provide a magnified view of the dental area of interest subject to certain controls as disclosed below. Head-mounted camera and display system 12, which includes a camera 22 and close-up display 24 mounted in a glasses frame 28, is worn by a user or dental practitioner as shown in FIG. 2. Head-mounted camera and display system 12 communicates wirelessly to a computer system 20, which includes a processor 14, display 16 and memory 18 as shown in FIG. 1.

Figure 3:
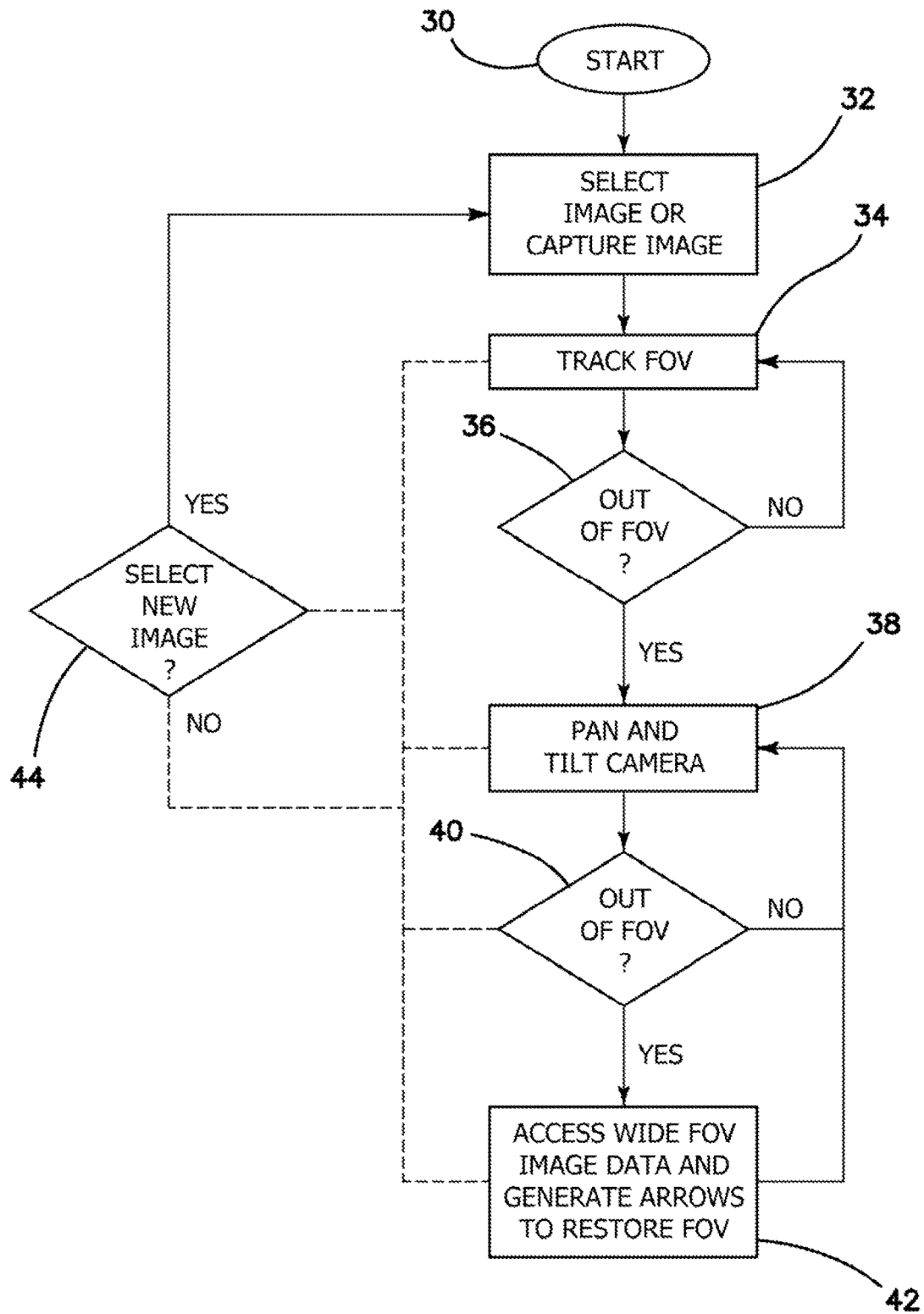
FIG. 3 is a flow diagram of the operation of the apparatus of FIGS. 1 and 2 according to the illustrated embodiments of the invention.

The user first turns on Google Glass 22 at step 30. Once the user acquires the desired view of the tooth or dental area of interest, he actuates image capture at step 32 in FIG. 3 with any kind of motion using a foot switch, orally or facially activated switch, finger flexure switch, uttering a word such as "capture", or blinking an eye or uploads a stored dental image from memory 18 by an appropriate command. Thereafter, an automatic tracking program in the computer system 20 to which the head mounted magnifying camera 22 is communicated, keeps the captured image in the center of the head-mounted display 24 in step 34. Image tracking programs are well known to the art.

Small movements of the camera 22 shifting the live field of view (FOV) as detected at step 36 can be automatically compensated by the tracking program to keep the live view matching the stored captured image in the center of the head display 24 as determined by an image identification program. For larger movements of the head that would tend to take the location of the desired captured image out of the field of live view of the camera 22, a conventional micro-pan and tilt mechanism (not shown) included in frame 28 and coupled to camera 22 or included in camera 22 and coupled to the lens of the camera 24 automatically moves the camera angle in step 38 to keep the location of the captured image in the live field of view of the camera 22 and hence in the center of the screen of the head-mounted display 24.

For extremely large movements that exceed the range of even the pan and tilt mechanism's ability to stay pointed at the location of the captured image as determined at step 40, the computer system 20 stored a wide field of view around the captured image at the time of actuation at step 32 in memory 18. This can be accomplished by a fast image capture of a wider field of view using conventional telescopic camera control included in camera 22. The wider field of view is taken in a fast enough frame shot at the time of image capture such that the user is unaware that the camera 22 has even taken the wide angle shot.

Alternatively, the camera 22 can be permanently adjusted to take high resolution wide angle shots. The captured image in the computer is thus a wide angle shot, but only the center of the high resolution live shot is displayed in the head-mounted display 24 in magnified scale under software control in processor 14.

After an extremely large movement taking the desired location out of the maximum field of view of the camera 22, an "out-of-frame" message or icon appears in the head-mounted display 24 at step 40. As the user returns the camera angle toward the original field of view, the live shot will begin to pick up parts of the image in the stored wide angle shot in memory 18 of the view of interest. An image recognition program in processor 14 at step 42 then directs the angle of the camera's pan and tilt mechanism to the direction of the location of the captured image, or displays directional arrows in the display 24 which cue the user to the direction in which the head mounted camera 22 needs to be turned in order to be once again be pointed at the desired location matching that of the captured image. Image recognition programs are well known in the art. The last view of the captured image may be maintained as a captured image in display 24 in such an instance. As soon as the live shot regains the location of the desired image, it is identified as such by the image recognition program in processor 14 and moved by the tracking program in processor 14 into the center of the display 24 and maintained there as long as it is in the live field of view of the camera 22.

The operator may move around, viewing the entire area or a different view, while the display screen 24 would still be showing a live view of the particular tooth or area in question. The displayed image would change since the camera angle is changing, but the area of interest would stay centered in the field of view, avoiding the need for the user to constantly hunting for the tooth or area by controlling his/her head position.

The captured image is released or erased by a deactivation command from the user at step 44, which is an interrupt that can be entered from any point in the program, which again could be made by any kind of motion or saying a word, such as "release". The computer system may also store multiple captured images which can be orally labeled by the user at the time of capture and reacquired at any time by calling out the file name of the stored captured image, such as by saying the name of the tooth. The user can thus go quickly back using the computer tracking and direction to a previously captured location without the need to recapture the location.

Record keeping in a database in memory 18 can also be easily achieved by similarly using oral commands from the user at step 32 to store any captured image into a patient record. Thus, well centered images of a tooth before, during and after any procedure may be captured and stored in a readily accessible patient record without the need to stop or delay the procedure for the purposes of making a photographic record.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A method comprising:
   providing a live view image of a dental area of interest using a head mounted imaging device subject to head movements of a predetermined amount or less;
   displaying the live image of the dental area of interest on a head-mounted display having a center of a field of view;
   actuating a first image capture of the dental area of interest subject to movement and downloading the first captured image of the dental area of interest into the a computer system communicated to the head mounted imaging device, or uploading a first image of a stored dental area of interest from the computer system;
   actuating a second image capture of the dental area of interest subject to movement and downloading the second captured image of the dental area of interest into the computer system communicated to the head mounted imaging device; and
   performing pattern recognition on the live image of the dental area of interest to keep the live image of the dental area of interest in the center or a selected position of the field of view of the head-mounted display notwithstanding movements of the head mounted imaging device of a predetermined amount or less and notwithstanding movements of the live image of the dental area of interest, where performing pattern recognition comprises:
      automatically tracking the live image of the dental area of interest in the computer system by comparing the live image of the dental area of interest with the first captured image of the dental area of interest in real time; and
      automatically tracking the live image of the dental area of interest in the computer system by comparing the live image of the dental area of interest with the second captured image of the dental area of interest in real time if the live image of the dental area of interest has exceeded a field of view of the first captured image of the dental area of interest.

2. The method of claim 1 further comprising automatically compensating for small movements of the head mounted imaging device shifting the center of or selected position in the field of view by using a tracking program in the computer system to keep the live image of the dental area of interest in the center or the selected position in the field of view of the head-mounted display.

3. The method of claim 2 further comprising:
   providing a micro-pan and tilt mechanism coupled to the head mounted imaging device or a lens of the head mounted imaging device for larger movements of a head that take the live image of the dental area of interest out of the center or selected position in the field of view beyond that which can be compensated by the tracking program; and
   automatically moving the head mounted imaging device angle using the micro-pan and tilt mechanism to keep the live image of the dental area of interest in the center of or the selected position in the field of view of the head-mounted display.

4. The method of claim 1 where automatically tracking the live image of the dental area of interest in the computer system comprises:
   providing a micro-pan and tilt mechanism coupled to the head mounted imaging device or a lens of the head mounted imaging device; and
   automatically moving the head mounted imaging device angle using the micro-pan and tilt mechanism to keep the live image of the dental area of interest in the center of or selected position in the field of view of the head-mounted display.

5. The method of claim 3 where the captured second image comprises a wide field of view around the live image of the dental area of interest that exceeds the range of the pan and tilt mechanism's ability to stay pointed at the live image of the dental area of interest, the method further comprising:
   storing the captured second image;
   displaying an "out-of-frame" message or icon in the head-mounted display;
   controlling the pan and tilt mechanism to direct the head-mounted imaging device to the live image of the dental area of interest and/or displaying directional arrows in the head-mounted display to cue a user to a direction in which the head-mounted imaging device needs to be turned in order to bring the live image of the dental area of interest toward the center of or selected position in the field of view by using an image recognition program in the computer system using the stored wide field of view around the live image of the dental area of interest;
   reacquiring at least a portion of the wide field of view around the image of the live image of the dental area of interest;
   identifying a desired live view of the dental area of interest by the image recognition program; and
   moving the desired live view of the dental area of interest into the center of or selected position in the field of view using the tracking program.

6. The method of claim 5 where storing the captured second image comprises taking and storing a fast image capture of an enhanced wide field of view using a telescopic camera control.

7. The method of claim 6 where storing the captured second image comprises storing the captured second image in a fast frame shot at the time of image capture during a time interval which is short enough so that the user does not perceive that the head-mounted imaging device has taken a telescopic enhanced wide field of view image.

8. The method of claim 5 where storing the captured second image comprises taking a high resolution wide angle image, but displaying only a center or selected portion of the high resolution wide angle image in the head-mounted display in a magnified view.

9. The method of claim 1 further comprising releasing or erasing either the first or second captured image by a deactivation command from a user.

10. An apparatus comprising:
a computer system with a memory;
a head mounted imaging device communicated with the computer system, the head mounted imaging device subject to head movements of a predetermined amount or smaller; and
a head-mounted display having a center of a field of view subject to movement and communicated with the computer system,
where the head mounted imaging device is configured to capture a first image of a dental area of interest and store it within the memory of the computer system,
where the imaging device is configured to capture a second image of a dental area of interest and store it within the memory of the computer system, and
where the computer system comprises pattern recognition means to automatically track a live image of the dental area of interest provided by the imaging device to keep it in the center of or a selected position in the field of view of the head-mounted display, the pattern recognition means comprising:
  means to compare the live image of the dental area of interest with the captured first image of the dental area of interest in real time; and
  means to compare the live image of the dental area of interest with the captured second image of the dental area of interest if the live image of the dental area of interest has exceeded a field of view of the first captured image of the dental area of interest.

11. The apparatus of claim 10 where the computer system automatically compensates for small movements of the head mounted imaging device shifting the center of or selected position in the field of view to keep the live image of the dental area of interest in the center of or selected position in the field of view of the head-mounted display by image tracking.

12. The apparatus of claim 11 further comprising:
a micro-pan and tilt mechanism coupled to the head mounted imaging device or a lens of the head mounted imaging device for larger movements of the head that take the live image of the dental area of interest out of the center of or selected position in the field of view beyond that which can be compensated by the tracking program; and
where the computer system automatically moves the head mounted imaging device angle using the micro-pan and tilt mechanism to keep the live image of the dental area of interest in the center of or selected position in the field of view of the head-mounted display by image tracking.

13. The apparatus of claim 10 further comprising:
a micro-pan and tilt mechanism coupled to the head mounted imaging device or a lens of the head mounted imaging device; and
where the computer system automatically moves the head mounted imaging device angle using the micro-pan and tilt mechanism to keep the live image of the dental area of interest in the center of or selected position in the field of view of the head-mounted display by image tracking.

14. The apparatus of claim 12 where the captured second image comprises a wide field of view around the live image of the dental area of interest that exceeds a range of the pan and tilt mechanism's ability to stay pointed at the live image of the dental area of interest, and
wherein the computer system displays an "out-of-frame" message or icon in the head-mounted display, controls the pan and tilt mechanism to direct the head-mounted imaging device to the live image of the dental area of interest and/or displays directional arrows in the head-mounted display to cue a user to a direction in which the head-mounted imaging device needs to be turned in order to bring the live image of the dental area of interest toward the center of or selected position in the field of view using image recognition on the captured second image comprising the wide field of view around the live image of the dental area of interest, reacquires at least a portion of the wide field of view around the live image of the dental area of interest, identifies the live image of the dental area of interest by image recognition, and moves the live image of the dental area of interest into the center of or selected position in the field of view by image tracking.

15. The apparatus of claim 14 where the computer system stores the captured second image by taking and storing a fast image capture of an enhanced wide field of view using a telescopic camera control.

16. The apparatus of claim 15 where the computer system takes and stores the fast image capture by taking a fast frame shot at the time of image capture during a time interval which is short enough so that the user does not perceive that the head-mounted imaging device has taken a telescopic enhanced wide field of view image.

17. The apparatus of claim 14 where the computer system stores captured second image by taking a high resolution wide angle image, but displaying only a center or selected portion of the high resolution wide angle image in the head-mounted display in a magnified view.

* * * * *